US00PP30930P2

(12) United States Plant Patent
Van Dijk

(10) Patent No.: US PP30,930 P2
(45) Date of Patent: Oct. 8, 2019

(54) ***ANTHURIUM* PLANT NAMED 'ANTHYTZEL'**

(50) Latin Name: ***Anthurium andraecmum* L.**
Varietal Denomination: ANTHYTZEL

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/932,636

(22) Filed: Mar. 28, 2018

(51) Int. Cl.
*A01H 5/02* (2018.01)

(52) U.S. Cl.
USPC ..... Plt./369

(58) Field of Classification Search
USPC ..... Plt./369
CPC ..... A01H 5/02
See application file for complete search history.

*Primary Examiner* — Keith O. Robinson
(74) *Attorney, Agent, or Firm* — Jondle & Associates, P.C.

(57) ABSTRACT

A new *Anthurium* plant named 'ANTHYTZEL' particularly distinguished by having shiny, red, orbicular cordate and very durable spathes that retain the original color for a very long period of time, dark green and ovate-cordate, durable leaves, white spadix with yellow tips, early and continuous flowering throughout the year, and a plant height of 35.0 cm to 40.0 cm is disclosed.

3 Drawing Sheets

Genus and species: *Anthurium andraeanum* L.
Variety denomination: 'ANTHYTZEL'.

BACKGROUND OF THE NEW PLANT

The present invention comprises a new and distinct variety of *Anthurium*, botanically known as *Anthurium andraeanum* L., and hereinafter referred to by the variety name 'ANTHYTZEL'. The new *Anthurium* plant is a product of a planned breeding program conducted by the inventor in Bleiswijk, the Netherlands. The objective of this breeding program was to create a new 35.0 cm to 40.0 cm height plant with shiny and blistered, red, orbicular cordate and very durable spathes.

The new variety originated from a cross-pollination made in September 2006 in Bleiswijk, The Netherlands. The female parent was a red *Anthurium* pot plant designated 'ANTHOLODOJ' (U.S. Plant Pat. No. PP20,254), and the male parent was a red *Anthurium* pot plant designated '10619-01' (unpatented).

A single plant was selected from the progeny of the stated cross in August 2008 and has been asexually reproduced repeatedly by tissue culture in Bleiswijk, The Netherlands over a 6-year period. The present invention has been found to retain its distinctive characteristics through successive asexual propagations.

Plant Breeder's Rights for this variety have been applied for in the European Union on Nov. 25, 2016. 'ANTHYTZEL' has not been made publicly available or sold anywhere in the world more than one year prior to the effective filing date of this application.

SUMMARY OF THE INVENTION

The following are the most outstanding and distinguishing characteristics of this new variety when grown under normal horticultural practices in Bleiswijk, The Netherlands:

1) Shiny and blistered, red, orbicular cordate spathes;
2) White spadix with yellow tips; and
3) Green, ovate cordate leaves.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 44-week old plant grown in a greenhouse in Bleiswijk, The Netherlands in February 2018. Colors in the photographs may differ from the color values cited in the detailed botanical description, which accurately describe the actual colors of the new variety.

DESCRIPTION OF THE NEW VARIETY

Figure 1:
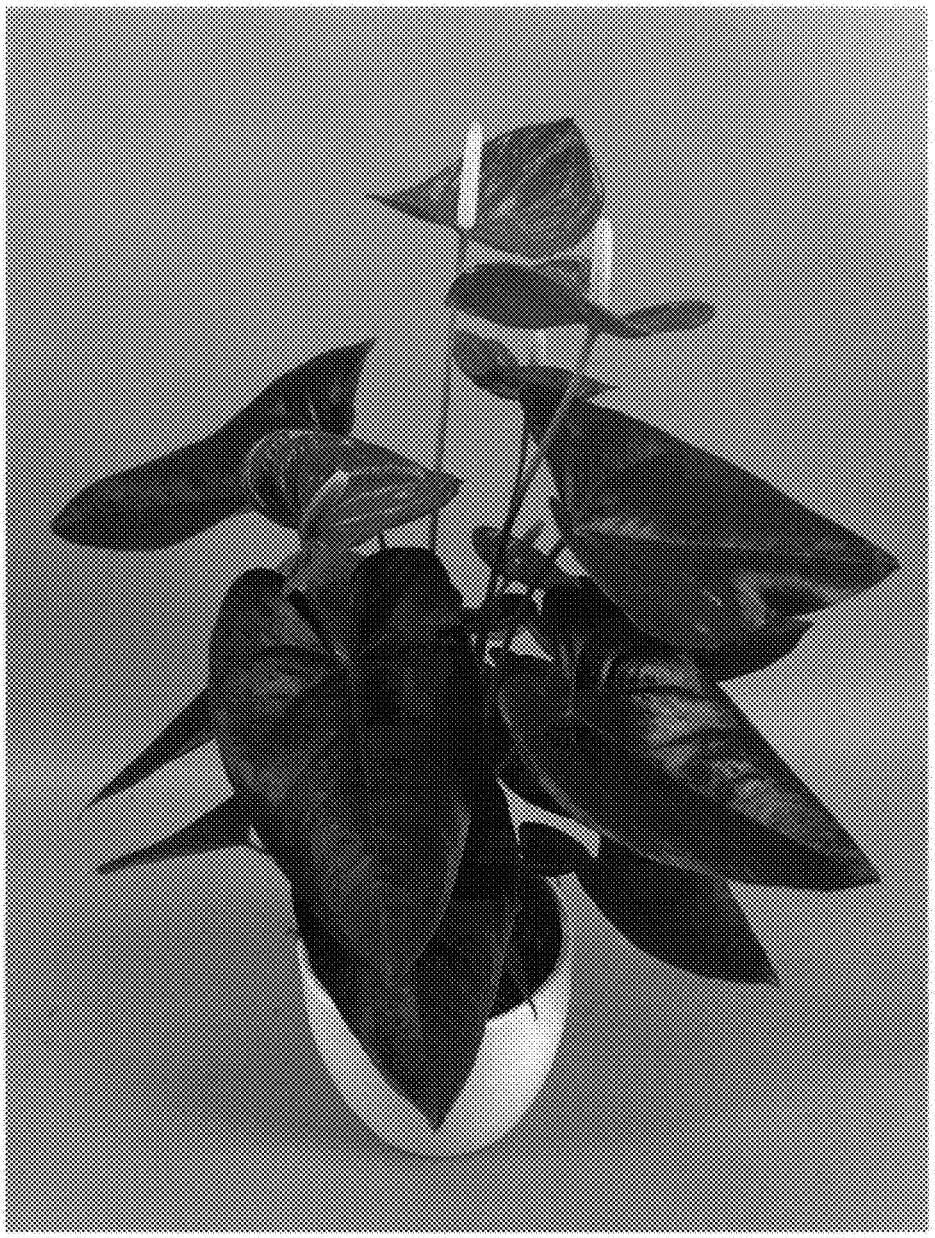
FIG. 1 shows the overall plant habit, including blooms and foliage.
Figure 2:
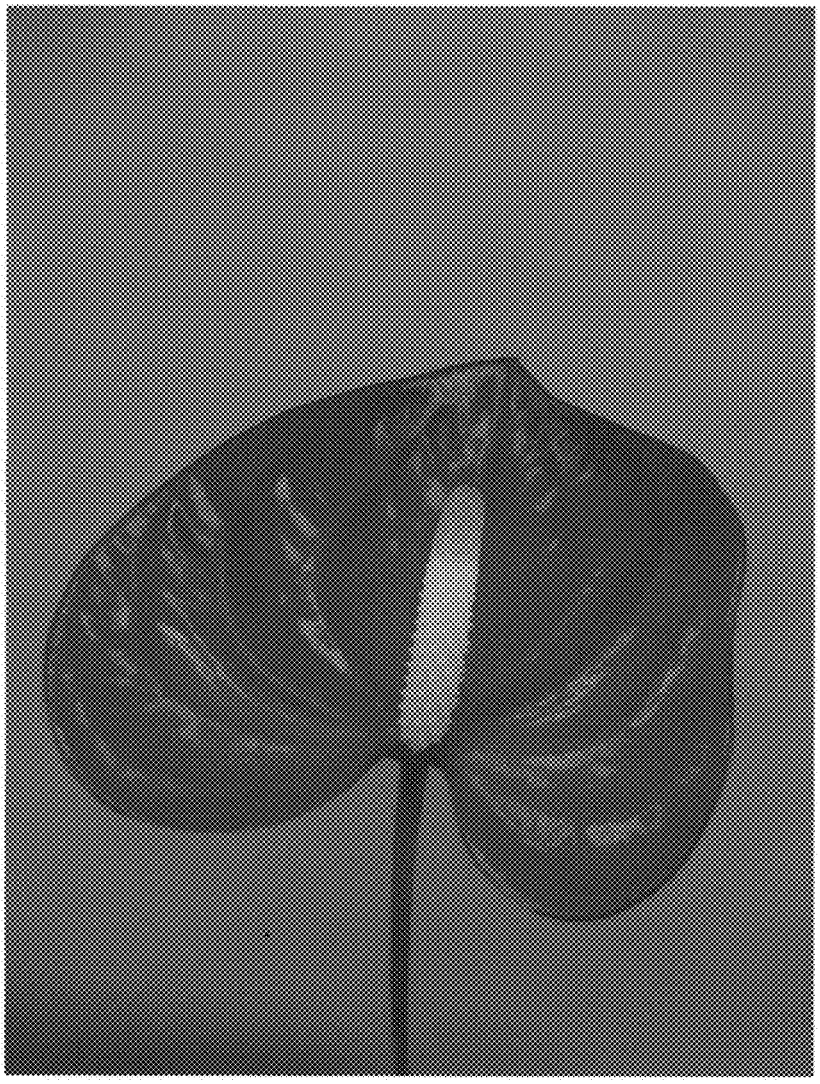
FIG. 2 shows a close-up of the mature spathe.
Figure 3:
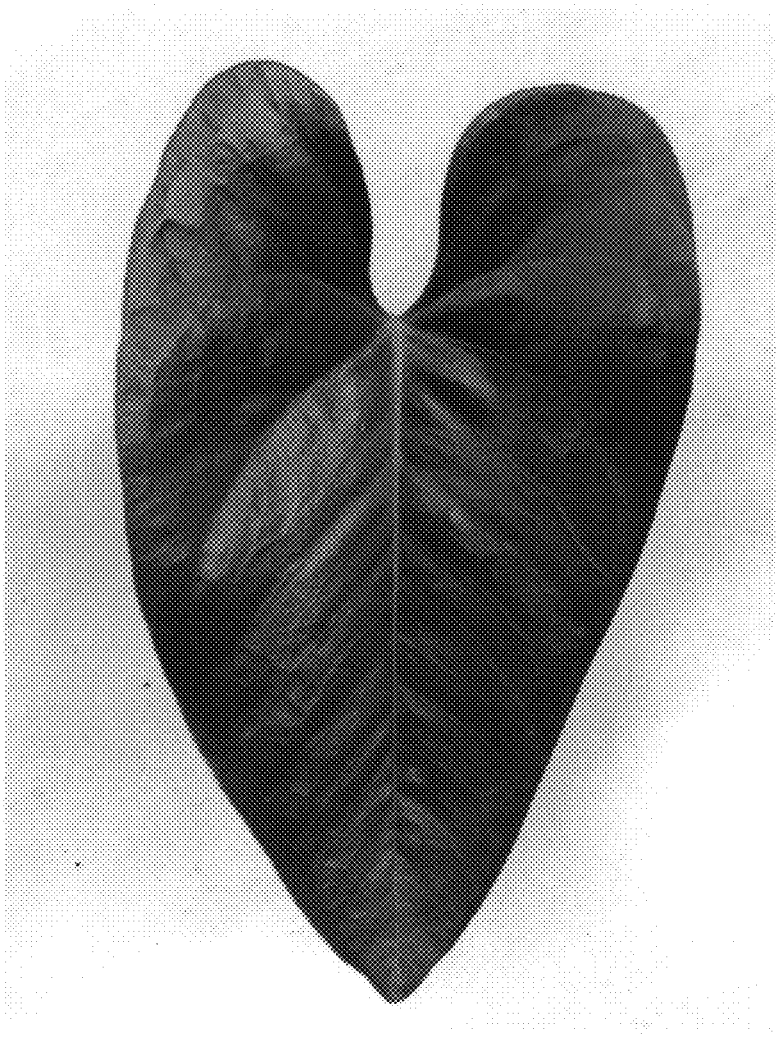
FIG. 3 shows a close-up of the upper leaf blade surface.

The following detailed description sets forth the distinctive characteristics of 'ANTHYTZEL'. The data which define these characteristics were collected from asexual reproductions carried out in Bleiswijk, The Netherlands. The plant history was taken on 44-week old plants which were planted from tissue culture in 14 centimeter (diameter) pots and grown in a glass greenhouse between 19° C. and 24° C. Observations were made in February 2018. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:
*Family.*—Araceae.
*Botanical.*—*Anthurium andraeanum* L.

*Common name.*—*Anthurium.*

*Denomination.*—'ANTHYTZEL'.

Parentage:

*Female parent.*—*Anthurium* plant 'ANTHOLODOJ' (U.S. Plant Pat. No. PP20,254).

*Male parent.*—*Anthurium* plant '10619-01' (unpatented).

Plant:

*Propagation.*—Tissue culture.

*Root description.*—Fleshy-creamy (RHS 160D) colored roots with small hairy lateral roots having greenish-yellow (RHS 4A) colored root tips.

*Time to produce a finished flowering plant.*—42 to 46 weeks after planting in a 14 cm (diameter) pot.

*Growth habit.*—Upright.

*Height* (*measured from soil, including inflorescence*).—35.0 cm to 40.0 cm.

*Width* (*measured from leaf tips*).—37.0 cm to 40.0 cm.

Leaves:

*Immature leaves.*—Length: 13.0 cm to 15.0 cm. Width: 8.0 cm to 9.0 cm. Color: Upper surface: RHS 146A. Lower surface: RHS 146B. Texture (both upper and lower surfaces): Shiny, leathery, thin and soft.

*Mature leaves.*—Length (fully expanded): 18.0 cm to 20.0 cm. Width: 10.5 cm to 11.5 cm. Shape: Ovate cordate. Apex: Acute. Base: Cordate. Leaf blade angle with the petiole: Between 90 degrees and 110 degrees Leaf margin: Entire. Color: Upper surface: RHS 147A. Lower surface: RHS 146B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 147B. Lower surface: RHS 146C.

*Lobes.*—Present. Arrangement: Leaf blade has two lobes extending past the petiole. The lobes are non-touching. Length of lobes of mature leaf blades: 3.0 cm to 4.0 cm. Width of lobes of mature leaf blades: 4.5 cm to 5.5 cm. Distance from petiole/leaf junction to highest point on lobes of mature leaf: 4.0 cm to 5.0 cm.

*Petiole.*—Cross-section: Round. Diameter: 0.3 cm to 0.4 cm. Length: 13.0 cm to 16.0 cm fora mature leaf size. Color: Mature leaf: RHS 144A. Immature leaf: RHS 144B. Cataphyll color surrounding the petiole: Outside: RHS 145B with red (RHS 182A) tip. Inside: RHS 145C with red (RHS 182B) tip.

*Geniculum.*—Length: 2.5 cm to 3.0 cm. Width: 0.4 cm to 0.5 cm. Color: RHS 144A/B.

Inflorescence:

*Arrangement.*—Single.

*Flowering habit* (*length of flowering season*).—Continuous.

*Number of inflorescences per plant.*—4 to 6.

*Fragrance.*—Absent.

*Longevity of inflorescence on plant.*—Over a year.

Spathe:

*Buds.*—The spathe is tightly rolled around the spadix and extrudes from the peduncle sheath. After the spathe is fully open, the peduncle elongates some extra centimeters.

*Arrangement.*—Spathe angle with the peduncle is between 100 degrees and 120 degrees; the spathe stands on a wiry peduncle about 7.0 cm to 9.0 cm above the foliage.

*Shape.*—Orbicular cordate.

*Apex.*—Mucronate.

*Base.*—Cordate.

*Texture.*—Shiny and blistered.

*Blistering.*—Medium to weak.

*Margin.*—Undulated.

*Size.*—Length: 9.0 cm to 10.0 cm. Width: 9.0 cm to 9.5 cm.

*Lobes.*—Present.

*Arrangement.*—The spathe has two lobes extending past the peduncle. The lobes are non-touching. Length: 2.0 cm to 2.5 cm. Width: 4.0 cm to 4.5 cm.

*Color.*—Just fully open: Upper surface: RHS N45A. Lower surface: RHS N45C. This red color remains for a very long period, at least more than 30 weeks after opening.

Peduncle:

*Shape.*—Erect.

*Cross-section.*—Round.

*Length.*—31.0 cm to 36.0 cm.

*Diameter.*—0.3 cm to 0.4 cm.

*Color.*—RHS 144B.

Flowering time:

*General.*—One small, rooted, untreated tissue culture plant of 8.0 cm tall will flower, depending on season, after 42 to 46 weeks and 4 to 5 blossoms appear. More blossoms appear after some additional weeks so that a full flowering and commercial plant will have 5 to 6 red spathes. Smaller blossoms may occur on immature plants.

Spadix:

*Size.*—Length: 3.5 cm to 4.5 cm (depending on flower size). Width (at apex): 0.5 cm to 0.6 cm. Width (at base): 0.6 cm to 0.7 cm.

*Shape.*—Columnar.

*Angle from spadix tip to peduncle.*—170 degrees to 180 degrees.

*Curvature of longitudinal axis.*—Straight.

*Texture.*—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color.*—Immature: RHS 14A. Mature: RHS NN155A. Ages to: RHS N144A.

Flowers:

*Quantity per spadix.*—170 to 220.

*Spadix flower arrangement.*—Bisexual, rounded in cross-section.

*Shape.*—Rounded.

*Size.*—Length: 0.05 cm to 0.10 cm. Diameter (maximum): 0.10 cm.

*Color.*—RHS 156D.

Reproductive organs:

*Stamens.*—Not visible.

*Pollen amount.*—Absent.

*Pistil.*—Quantity: 170 to 220. Length: Less than 0.01 cm. Color: RHS 156D.

*Style.*—Not observed to date.

*Stigma.*—Shape: Ovoid. Diameter: Less than 0.01 cm. Color: RHS 156D.

*Ovary.*—Rarely visible.

*Ovary color.*—Not measured.

Fruit and seed set: None observed to date.

Disease and pest resistance: No specific resistance or susceptibility observed to pathogens or pests common to *Anthurium* under commercial conditions.

COMPARISON WITH PARENTAL AND COMMERCIAL VARIETIES

'ANTHYTZEL' differs from the female parent plant 'ANTHOLODOJ' (U.S. Plant Pat. No. PP20,254) in that 'ANTHYTZEL' has ovate-cordate leaves and a wide spadix angle to the spathe, whereas 'ANTHOLODOJ' has elliptical cordate leaves and a medium spadix angle to the spathe. Additionally, 'ANTHYTZEL' has a spathe arrangement in which the distance between the highest flower and the highest leaf is 7.0 cm to 10.0 cm above the foliage, whereas the distance for 'ANTHOLODOJ' is 4.0 cm to 7.0 cm above the foliage.

'ANTHYTZEL' differs from the male parent plant '10619-01' (unpatented) in that 'ANTHYTZEL' has ovate-cordate leaves, a wide spadix angle to the spathe, a mucronate spathe apex, and green cataphyll with red tips, whereas '10619-01' has elliptical cordate leaves, a medium spadix angle to the spathe, a narrow acuminate spathe apex, and red cataphyll. Additionally, 'ANTHYTZEL' has a spathe arrangement in which the distance between the highest flower and the highest leaf is 7.0 cm to 10.0 cm above the foliage, whereas the distance for '10619-01' is 5.0 cm to 8.0 cm above the foliage.

'ANTHYTZEL' differs from similar commercial variety 'ANTHDASZUM' (U.S. Plant patent application Ser. No. 15/731,361) in that 'ANTHYTZEL' has green cataphyll with red tips and ovate-cordate leaves, whereas 'ANTHDASZUM' has red-orange cataphyll and narrow long cordate leaves. Additionally, 'ANTHYTZEL' has shorter spadix than 'ANTHDASZUM'.

'ANTHYTZEL' differs from similar commercial variety 'ANTHABUDON' (U.S. Plant Pat. No. PP20,282) in that 'ANTHYTZEL' has green cataphyll with red tips, ovate-cordate leaves, and orbicular cordate spathes, whereas 'ANTHABUDON' has red cataphyll, elliptical cordate leaves, and oblong cordate spathes.

I claim:

1. A new and distinct variety of *Anthurium* plant named 'ANTHYTZEL', substantially as illustrated and described herein.

* * * * *